United States Patent [19]

Osadca

[11] 4,277,248
[45] Jul. 7, 1981

[54] METHODS FOR THE DETECTION OF LOW LEVEL CONCENTRATIONS OF SULFONAMIDES

[75] Inventor: Modest Osadca, Passaic, N.J.

[73] Assignee: Hoffmann-La Roche Inc., Nutley, N.J.

[21] Appl. No.: 68,820

[22] Filed: Aug. 22, 1979

[51] Int. Cl.³ .................. G01N 33/02; G01N 31/22
[52] U.S. Cl. ........................... 23/230 M; 23/230 R
[58] Field of Search ....................... 23/230 R, 230 M

[56] References Cited

PUBLICATIONS p-Dimethylcinnamaldehyde as a Spray Reagent for Sulfonamides in Combined Avicel-Kieselguhr TLC, Lee, J. Chrom., vol. 93621, pp. 480-484.

Primary Examiner—Michael S. Marcus
Attorney, Agent, or Firm—Jon S. Saxe; George M. Gould; William M. Farley

[57] ABSTRACT

Methods for the determination of low levels of sulfonamides, and, in particular, sulfadimethoxine, in poultry feeds are disclosed.

6 Claims, No Drawings

METHODS FOR THE DETECTION OF LOW LEVEL CONCENTRATIONS OF SULFONAMIDES

BACKGROUND OF THE INVENTION

In animal husbandry, drug cross-contamination of animal feeds in feed mixing processes is a serious problem. Such drug carry-over is known to occur even when good manufacturing practices are followed.

Since sulfonamides are often used as poultry food additives, they are often involved in cross-contamination problems. For example, sulfadimethoxine [N'(2,6-dimethoxy-4-pyrimidinyl)sulfanilamide] is effective; both alone and in combination with a potentiator, e.g. 2,4-diamino-5(4', 5'-dimethoxy-2'-methylbenzyl)pyrimidine; in poultry feeds as an anticoccidial and antibacterial agent.

There is, thus, a need for a rapid method of detecting and estimating low levels of sulfadimethoxine in poultry feeds and, especially, in withdrawal feeds, i.e. feeds not containing the sulfadimethoxine but prepared using feed processing equipment which had been used for the preparation of sulfadimethoxine-containing feedstuff.

Such tests must also be suitable for use in detecting low-levels of sulfonamides in poultry feeds containing other feed additives such as, for example, amprolium, bacitracin, clopidol, erythromycin, epronidazols, lasalocid sodium (Avatec ®), monensin sodium (Coban ®), ormethoprim, trimethoprim and the like.

The Bratton-Marshall reaction is used in many assay procedures to determine sulfa drugs in poultry feeds. After extraction of the sample and purification of the extract, the extract containing a sulfa drug is then subjected to the Bratton-Marshall reaction. The Bratton-Marshall reaction consists of:

(a) acidification of the extract;
(b) reaction of the primary amine of a sulfonamide with a nitrite;
(c) decomposition of excess nitrite with sulfamic acid; and
(d) reaction of the diazotized amine with a coupling reagent (a chromogen, e.g., N-(1-naphthyl)-ethylenediamine dihydrochloride, to form a wine-red colored complex and
(e) determination of the sulfonamide concentration from the resulting colored complex.

This test, since it involves extraction and purification of an extract with subsequent acidification, diazotization, decomposition of excess nitrite and coupling is too elaborate and unwidely for a rapid field test.

A test suitable for rapid detection of a sulfonamide in the field involves the colorimetric reaction of Ehrlich reagent (an acidified methanolic solution of a chromogen, p-dimethylamino-benzaldehyde) with a sulfonamide. The Ehrlich reagent, which is also used as a spray reagent in thin layer chromatography (TLC), forms mostly yellow-colored Schiff bases upon reaction with the primary amines of sulfa drugs and/or their degradation products.

However, in this test, a yellow color can also result from interfering substances, e.g., other drugs or additives in feedstuff.

There, is, therefore, a definite need for a rapid, accurate test for sulfonamides in feedstuff which test is not deleteriously affected by the presence of interfering substances therein.

SUMMARY OF THE INVENTION

This invention relates to a color reaction method for the determination of low levels of sulfonamides; and, especially, sulfadimethoxine; in feedstuff. This method involves use of p-dimethylaminocinnamaldehyde as a chromogen to increase the resulting color intensity and to shift the resulting color wavelength to the red.

DETAILED DESCRIPTION OF THE INVENTION

The colorimetric method encompassed by this invention involves the coupling, under specified reaction conditions, of a sulfonamide with p-dimethylaminocinnamaldehyde to form a red-colored Schiff base. Since the background interference from the various feed additives absorb in the yellow wavelength region, this method avoids such deleterious interference.

p-Dimethylamino-cinnamaldehyde, is a known chemical of commerce. The increased carbon chain length (CH=CH) between the resonance terminals of this chromogen, as compared to the p-dimethylaminobenzaldehyde chromogen of the Ehrlich reagent, results in a tenfold increase in color intensity (and, thus, in test sensitivity) as well as a shift of color to the red wavelength. Table I below lists comparative data for Ehrlich reagent and p-dimethylaminocinnamaldehyde reagent (PDMACA).

TABLE I

| Reagent | TLC SDM Detection Limit by Visual Evaluation | Test Tube Reaction Absorbance of SDM(10 mcg/ml) by Evelyn Colorimeter |
|---|---|---|
| Ehrlich | 100 ng | 0.060 (max. 450) |
| PDMACA | 10 ng | 0.560 (max. 545) |

The reaction of a sulfonamide with p-dimethylaminocinnamaldehyde is the basis for field tests to determine low levels of sulfonamides in poultry feeds. Two assay variations have been developed to test for sulfonamides in the presence of other, possibly interfering, additive in poultry feed.

One assay variation involves a visual evaluation which is semiquantitative in nature. In this procedure, a thin layer of a feed sample, sandwiched between filter papers, is wetted with a spray of the chromogen. After the upper sheet of filter paper is pressed firmly against the wetted feed, the appearance of wine-red colored spots indicates the presence of a sulfonamide.

In the second variation, a feed sample, in a centrifuge tube, is treated to extract any sulfonamide present. The extract is then mixed, in another centrifuge tube, with a chromogen solution. The appearance of a red color, visually observed, indicates the presence of a sulfonamide.

Sulfonamides which can be detected in low-levels in poultry feed include sulfadimethoxine, sulfadoxine, sulfamethoxazole, sulfisoxazole, sulfaquinoxaline, sulfaquanidine, sulfamethizole, sulfathiozole, sulfamerazine, sulfamilamide, sulfamethazine, sulfadiazine and the like.

The following Examples illustrate the invention.

EXAMPLE 1

This test illustrates the utility of p-dimethylaminocinnamaldehyde in detecting low levels of sulfadimethoxine in feedstuff.

A 0.5%(weight/volume) color reagent is prepared by dissolving 250 mg of p-dimethyl-aminocinnamaldehyde in 50 ml of methanol which contains 2 ml. of concentrated (ca. 36%) HCl.

10 grams of feed are spread on a sheet of filter paper (Whatman No. 1, 18.5 cm. diameter) so as to form a thin layer of approximately 16 cm. diameter. Mash feed can be used "as is" but pelleted feed must be ground to pass through a No. 20 sieve. The feed sample is covered with another sheet of filter paper. The feed-filter paper assembly is then uniformly wetted by spraying with 2 ml of the 0.5% color reagent solution of p-dimethylaminocinnamaldehyde.

The top sheet of filter paper is pressed down upon the feed layer. After about 30 seconds, wine-red spots on the top sheet of filter paper indicates the presence of sulfadimethoxine.

The test is semiquantitative in nature. With 62.5 ppm of sulfadimethoxine in the feed, more that 200 wine-red spots appeared on the filter paper. With 2 ppm of sulfadimethoxine, 3–6 spots appeared while at the 1 ppm level of sulfadimethoxine, 2–3 wine-red spots developed.

This test gives positive results with, primary aliphatic, aromatic, heterocyclic and cyclic amines.

The following feed additives, at the 100 ppm level in poultry feed, were tested in the above procedure and did not interfere with the detection of low levels of sulfadimethoxine:
  Amprolium
  Clopidol
  Decoquinate
  Erythromycin
  Furazolidine
  Ipronidazole (Ipropran ®)
  Lasalocid sodium (Avatec ®)
  Ethoxyquin (at 20 ppm)
  Lincomycin
  Monensin sodium(Coban)
  Neomycin
  Nystatin
  Ormetoprim
  Robenidine
  Roxarsone
  Trimithoprim.

Feed additives, at the 100 ppm level, which did interfere with this assay for sulfadimethoxine in poultry feed were:
  Bacitracin
  Carbarsone
  Cathomycin
  Chlortetracycline
  Flavomycin
  Ethoxyquin (EMG)
  Gentian violet
  Penicillin

EXAMPLE 2

This Example illustrates an alternate method, using p-dimethylaminocinnamaldehyde, to determine the presence of low levels of sulfadimethoxine in feedstuff in the presence of feed additives known to cause interference in the assay procedure described in Example 1.

A 0.125% (weight/volume) color reagent is prepared by dissolving 125 mg. of p-dimethylaminocinnamaldehyde in 100 ml. of methanol containing 2 ml. of concentrated (ca. 36%) HCl.

Approximately 10 g of poultry feed are placed in a 50 ml., glass-stopper centrifuge tube. 20 ml. of acetone, 4 ml. of 40% of Na OH and about 4 g of anhydrous $Na_2SO_4$ are added to the feedstuff in the tube, mixed thoroughly and then stirred. The centrifuge tube is stoppered, shaken for five minutes on a mechanical stirrer and then centrifuged for five minutes at 2200 rpm. The clear extract is decanted into another centrifuge tube and a Na OH pellet is added. The tube is stoppered and shaken for five minutes. 2 g of anhydrous $Na_2SO_4$ are added, and briefly hand-shakened. The contents are then centrifuged.

The clear extract is decanted into another centrifuge tube and 5 ml of the 0.125% color reagent are added. After mixing, a red color, indicating the presence of sulfadimethoxine, will develop after about 1 minute.

This procedure is suitable for the detection of levels of sulfadimethoxine down to about 2 parts per million.

The following poultry feed additives, at the 100 ppm level, were tested in the above procedure and did not interfere with the detection of low levels of sulfadimethoxine:
  Amprolium
  Arsanilic acid
  Bacitracin
  Carbarsone
  Cathomycin
  Clopidol
  Decoquinate
  Erythromycin
  Flavomycin
  Furazolidine
  Ipronidazole (Ipropan ®)
  Lasalocid sodium (Avatec ®)
  Lincomcin
  Monensin sodium (Coban)
  Neomycin
  Nestatin
  Ormethprim
  Robenidine
  Ronidazole
  Roxarsone
  Trimethoprim
  Virginiamycin.

In addition, gentian violet at the 20 ppm level and ethoxyquin (EMQ) at 155 ppm do not interfere with this assay of sulfadimethoxine. However, both chlortetracycline and penicillin at the 100 ppm level did interfere with the assay for sulfadimethoxine in poultry feed. Further, other sulfonamides as well as compounds with a primary amino group, and with solubility characteristics similar to sulfadimethoxine, will interfere with this assay procedure.

I claim:

1. A method for the determination of low levels of sulfonamides in poultry feeds which comprises.
   (a) forming a thin layer of the feed on a filter paper substrate,
   (b) placing a filter paper cover over the feed layer,
   (c) uniformly wetting the resulting filter paper/feed unit with a spray of a chromogen solution comprising p-dimethylaminocinnamaldehyde in acidified methanol,
   (d) applying a uniform pressure to the entire unit surface and
   (e) visually observing any wine-red spots which develop on the filter paper cover to determine the presence of a sulfonamide in the poultry feed.

2. The method of claim 1 wherein the sulfonamide is sulfadimethoxine.

3. The method of claim 1 wherein the chromogen solution is a 0.5% weight/volume solution of p-dimethylaminocinnamaldehyde in acidified methanol.

4. A method for the determination of low levels of sulfonamides in poultry feed which consists essentially of
(a) admixing an aliquot of the poultry feed with acetone sodium hydroxide solution and disodium sulfate;
(b) centrifuging the above admixture;
(c) decanting the resulting clear extract from (b), adding thereto sodium hydroxide and disodium sulfate and, after shaking, centrifuging the admixture;
(b) decanting the clear extract from (c) and adding thereto a chromogen solution comprising p-dimethylaminocinnamaldehyde in acidified methanol and
(e) visually observing the development of a red color to determine the presence of a sulfonamide in the poultry feed.

5. The method of claim 4 wherein the sulfonamide is sulfadimethoxine.

6. The method of claim 4 wherein the chromogen solution is a 0.125% weight/volume solution of p-dimethylaminocinnamaldehyde in acidified methanol.

* * * * *